United States Patent [19]

N'Guyen

[11] Patent Number: 5,431,912
[45] Date of Patent: Jul. 11, 1995

[54] COSMETIC OR DERMOPHARMACEUTICAL COMPOSITION CONTAINING, IN COMBINATION, A LAUROYLMETHIONATE OF A BASIC AMINO ACID AND AT LEAST ONE POLYPHENOL

[75] Inventor: Quang L. N'Guyen, Antony, France

[73] Assignee: L'Oreal, Paris, France

[21] Appl. No.: 136,832

[22] Filed: Oct. 18, 1993

[30] Foreign Application Priority Data

Oct. 22, 1992 [FR] France ................... 92 12654

[51] Int. Cl.⁶ .............. A61K 7/02; A61K 7/027; A61K 7/032; A61K 7/48
[52] U.S. Cl. ..................... 424/401; 424/59; 424/63; 424/64; 424/65; 424/195.1; 424/450; 424/DIG. 5; 514/468; 514/569; 514/844; 514/845; 514/846; 514/847; 514/937
[58] Field of Search ............... 424/401, 450, DIG. 5, 424/195.1; 514/844, 845, 846, 847, 59, 63, 64, 65, 847, 937, 468, 569

[56] References Cited
FOREIGN PATENT DOCUMENTS

| | | |
|---|---|---|
| 0275005 | 7/1988 | European Pat. Off. . |
| 0307626 | 3/1989 | European Pat. Off. . |
| 0353161 | 1/1990 | European Pat. Off. . |
| 0500332 | 8/1992 | European Pat. Off. . |
| 1603799 | 7/1971 | France . |
| 2400358 | 3/1979 | France . |

*Primary Examiner*—Jyothsna Venkat
*Attorney, Agent, or Firm*—Oliff & Berridge

[57] ABSTRACT

The present invention addresses a cosmetic or dermopharmaceutical composition comprising, in a suitable vehicle, an antioxidizing system possessing a synergic effect consisting of the combination of laroylmethionate of lysine, histidine or arginine, and of at least one polyphenol chosen from:

a) a derivative of (2,5-dihydroxyphenyl)-carboxylic acid, a homologue or a corresponding salt,
b) an ester or amide of caffeic acid,
c) a flavonoid or an extract containing flavenoids, and
d) a rosemary extract containing diphenols, and their mixtures. The use of the antioxidizing system enables good preservation of compositions containing oxidation-sensitive fats.

7 Claims, No Drawings

COSMETIC OR DERMOPHARMACEUTICAL COMPOSITION CONTAINING, IN COMBINATION, A LAUROYLMETHIONATE OF A BASIC AMINO ACID AND AT LEAST ONE POLYPHENOL

The subject of the invention is a cosmetic or dermopharmaceutical composition containing, as antioxidizing agent, a combination possessing a synergic effect of a lauroylmethionate of a basic amino acid and of at least one polyphenol.

The majority of cosmetic or dermopharmaceutical compositions consist of a fatty phase, the oily products of which have a certain tendency to oxidize, even at room temperature. The consequence of this oxidation is to profoundly modify the properties, especially olfactory, thereof, which makes them unusable after a variable time period.

In order to protect the compositions with respect to these oxidation phenomena, it is common practice to incorporate protective agents which act as antioxidizing agents.

Among the most commonly used antioxidizing products, there may be mentioned ascorbic acid, which acts in particular by direct absorption of oxygen, but it has, however, the disadvantage of being very sparingly soluble in fats, which consequently does not enable them to be well protected.

With a view to overcoming the disadvantages of ascorbic acid, various antioxidizing systems have been recently proposed, in particular in French Patent No. 90 11384 (2,666,809), the latter consisting of at least one tocopherol or tocopherol derivative and at least one non-thiolated polypeptide.

Likewise, in French Patent No. 88 10295 (2,634,779), it has been suggested to use an antioxidizing system consisting of a tocopherol or a mixture of tocopherols, or of caffeic acid or one of its derivatives, of at least one complexing agent and of at least one non-thiolated polypeptide.

These antioxidizing systems have a particularly pronounced synergic effect, but they are nevertheless prone to pose problems of preservation during lengthy storage periods.

If the antioxidizing agents are particularly useful for the correct preservation of the fats in cosmetic or dermopharmaceutical compositions, it is also acknowledged that the latter, in certain applications, can also make it possible to efficiently combat the harmful effects of peroxides, especially organic peroxides formed by the action of atmospheric pollutants and of ultraviolet radiation.

Living cells have in fact various natural means of defence against lipid peroxides, in particular epidermal glutathione peroxidase, but its detoxifying efficiency is greatly reduced under the influence of exposure to ultraviolet radiation.

It is therefore important to be able to have available antioxidizing agents capable of inhibiting the formation of free radicals which are a source of oxidation phenomena which can cause irreversible cell damage.

After various studies on a large number of substances, it was unexpectedly observed that it was possible both to obtain good preservation of cosmetic or dermopharmaceutical compositions containing easily oxidizable fats and, moreover, to efficiently protect cutaneous lipids by using an antioxidizing system possessing a synergic effect consisting of a lauroylmethionate of a basic amino acid and of at least one polyphenol.

The subject of the invention is thus a cosmetic or dermopharmaceutical composition containing, in a suitable vehicle, an antioxidizing system possessing a synergic effect consisting of the combination of a lauroylmethionate of lysine, histidine or arginine and of at least one polyphenol selected from:

a) a derivative of (2,5-dihydroxyphenyl)carboxylic acid, a homologue or a corresponding salt, b) an ester or amide of caffeic acid, c) a flavonoid or an extract containing flavonoids, and d) a rosemary extract containing diphenols, and their mixtures.

Among the lauroylmethionates, it is very particularly preferred to use according to the invention L-lysine lauroylmethionate (MW=477.7) sold by the Company Givaudan Lavirotte.

Derivatives of (2,5-dihydroxyphenyl)carboxylic acid, their homologues and their salts are known compounds which have been described especially in French Patents 78.24174 (2,400,358) and 78.24175 (2,400,359).

These derivatives of (2,5-dihydroxyphenyl)carboxylic acid can be represented by the following general formula:

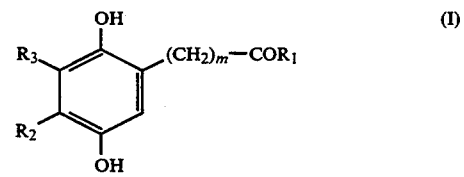

(I)

in which:

R$_1$ represents OR$_4$, OH or

R$_4$ represents a linear or branched C$_1$–C$_{20}$ alkyl radical, a linear or branched C$_2$–C$_{20}$ alkenyl radical or a C$_1$–C$_{20}$ alkyl radical substituted by one or a number of hydroxyl or alkoxy groups, r' and r" which are identical or different, represent a hydrogen atom, a C$_1$–C$_{20}$ alkyl radical, a C$_2$–C$_6$ hydroxyalkyl radical or a C$_3$–C$_6$ polyhydroxyalkyl radical or r' and r", taken together, form with the nitrogen atom a heterocycle, m is 1 or 2, (i) when m is 1, at least one of the R$_2$ and R$_3$ radicals represents a linear or branched C$_1$–C$_4$ alkyl radical, the other optionally representing a hydrogen atom, (ii) when m is 2, R$_2$ and R$_3$, which are identical or different, represent a hydrogen atom or a linear or branched C$_1$–C$_4$ alkyl radical.

Among the particularly preferred compounds of general formula (I), it is possible in particular to mention methyl 2,5-dihydroxy-4-methylphenylacetate.

Among the esters of caffeic acid, it is possible in particular to mention the compounds of formula (II):

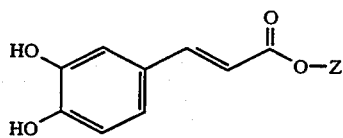

(II)

in which Z represents a $C_1$-$C_8$ alkyl, for example methyl, or the residue of a phytol.

Among the amides of caffeic acid, it is possible in particular to mention the compounds of formula (III):

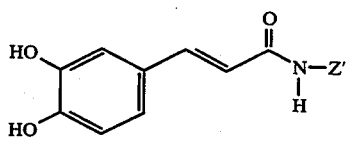

(III)

in which Z' represents a $C_1$-$C_8$, in particular $C_1$-$C_8$, alkyl.

The compounds of formula (II) or (III) are known or can be prepared according to known methods.

Among the flavonoids, it is possible to mention those corresponding to the two following general formulae:

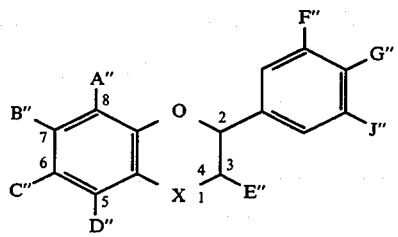

(IV)

in which:

A', B', C' and D', independently of one another, represent H or OH;

E' represents H, OH or OX', where X' represents:

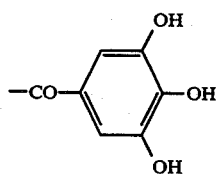

F', G', J' represent, independently of one another, H or OH; and $X_1$ represents —$CH_2$—, —CO— or —CHOH—, with the proviso that at least two of the radicals A" to G" or J" represent OH or that the E" radical represents OX', and

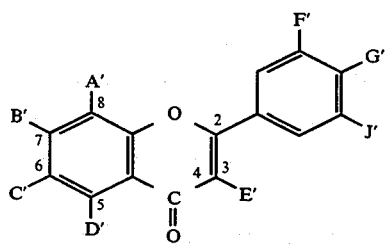

(V)

in which:

A', C' and D', independently of one another, represent H, OH or $OCH_3$;

E' represents H, OH or OR', where R' represents the residue of a sugar of formula R'OH;

B', F', G' and J', independently of one another, represent H, OH, $OCH_3$ or —$OCH_2$—$CH_2$—OH, with the proviso that at least two of the radicals A' to G' or J' represent OH.

Among the sugars R'OH, it is possible to mention rutinose.

The compounds of formula (IV) and (V) are known. They can be obtained in particular according to the processes described in "The Flavonoids", Harborne J. B., Mabry T. J., Helga Mabry, 1975, pages 1 to 45.

Among the flavonoids which can be used according to the invention, mention will in particular be made of taxifolin, catechin, epicatechin, eriodictyol, naringenin, rutin, troxerutin, chrysin, tangeretin, luteolin, epigallocatechin and epigallocatechin gallate, quercetin, fisetin, kaempferol, galangin, gallocatechin and epicatechin gallate.

Such compounds are found, in particular, in green tea extracts sold under the name "Sunphenon" by the Company Nikko.

The rosemary extract which can be used according to the invention, is essentially characterized by containing carnosic acid and carnosol and is obtained, for example, either by extraction followed by distillation (Chang et al. JOSC, Vol. 61, N° 6, June 1984), or by extraction with a polar solvent such as ethanol preceded by extraction using a non-polar solvent such as hexane to remove the odorant substances, as described in Patent Application EP-307,626.

Carnosic acid and carnosol are responding to the following formulae:

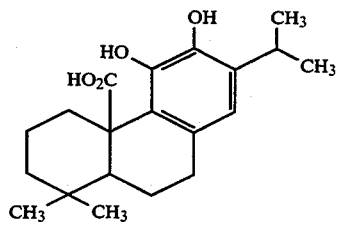

Carnosic acid

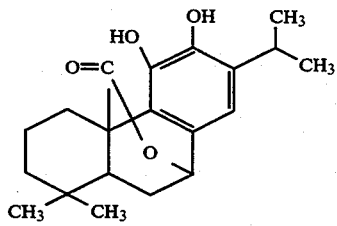

Carnosol

In the cosmetic or dermopharmaceutical compositions according to the invention, the lauroylmethionate of lysine, histidine or arginine is generally present at a concentration between 0.02% and 5% by weight with respect to the total weight of the composition.

The polyphenol as defined above is present in a proportion between 0.005 and 5% by weight with respect to the total weight of the composition. The ratio by weight of the basic amino acid lauroylmethionate to the polyphenol is generally between 20/80 and 90/10.

When the polyphenol is a derivative of (2,5-dihydroxyphenyl)carboxylic acid as represented by the general formula (I), the latter is preferably present at a concentration between 0.05 and 1%.

If the latter is an ester or amide of caffeic acid, the concentration is preferably between 0.05 and 2% by weight with respect to the total weight of the composition.

Finally, when a flavonoid, or extract containing flavonoids, is used, the latter is generally present at a concentration between 0.1 and 5% by weight with respect to the total weight of the composition.

Similarly, when a rosemary extract containing carnosic acid and carnosol is used, the latter is generally present at a concentration between 0.1 and 5% by weight with respect to the total weight of the composition.

The compositions according to the invention can be of very varied nature but are more particularly those containing oxidation-sensitive fats in a variable proportion, preferably between 0.1 and 99% by weight.

The fats present in the compositions according to the invention are, for example, fats of animal origin such as cetin (spermaceti), beeswax, lanolin, perhydrosqualene, turtle oil, and the like; plant fats in the form of oils, fats or waxes, such as sweet almond oil, avocado oil, olive oil, sesame oil, or macadamia oil; optionally hydrogenated coconut or palm kernel oils, cocoa butter, carnauba wax, or montan wax; and synthetic oils consisting of esters and/or ethers of glycerol or of glycol such as, for example, those described in French Patents No. 75.24656(2,281,916), 75.24657(2,281,743) and 75.24658(2,281,744).

In addition to more or less oxidizable fats, the cosmetic or dermopharmaceutical compositions according to the invention can also contain oxidation-sensitive products such as, for example, vitamin F or $\beta$-carotene.

The cosmetic or dermopharmaceutical compositions according to the invention are provided in particular in the form of oily solutions, of water-in-oil or oil-in-water emulsions, of optionally anhydrous solid products, of lotions or of microdispersions, or of vesicular dispersions, it being possible for the constituent lipids of the vesicles to be of ionic or nonionic type or else a mixture of these. The compositions according to the invention can also be provided in the form of milks for skin care, of Creams (creams for the face, for the hands, for the body, anti-sun creams, make-up-removing creams, foundation creams), liquid foundations, make-up-removing milks, anti-sun milks, bath oils, lipsticks, eye-shadows, deodorant sticks, and the like.

For topical application, the cosmetic or dermopharmaceutical compositions according to the invention comprise the vehicles and ingredients necessary to make it possible to present the composition, for example, in the salve, cream, milk, ointment or oily solution forms.

According to a preferred embodiment, the cosmetic or dermopharmaceutical compositions are provided in a form intended to be applied topically, in particular in the cream form intended to protect the lipids of the skin from oxidation.

The cosmetic and dermopharmaceutical compositions according to the invention can additionally contain various standard additives or ingredients, such as surface-active agents, dyes, fragrances, astringent products, products absorbing ultraviolet radiation, or organic solvents.

These cosmetic or dermopharmaceutical compositions are obtained according to conventional methods.

A number of examples of cosmetic and dermopharmaceutical compositions according to the invention will now be given by way of illustration.

| | % |
|---|---|
| EXAMPLE 1: Moisturizing cream | |
| Lysine lauroylmethionate | 1.15 |
| Methyl 2,5-dihydroxy-4-methylphenylacetate | 1.0 |
| Mg lanolate | 3.0 |
| Lanolin alcohol | 5.0 |
| Paraffin oil | 27.0 |
| Paraffin jelly | 15.0 |
| Methyl parahydroxybenzoate | 0.2 |
| Propyl parahydroxybenzoate | 0.1 |
| Demineralized water q.s. for | 100 |
| EXAMPLE 2: Protective day cream | |
| Lysine lauroylmethionate | 1.3 |
| Quercetin | 0.5 |
| Rosemary extract | 1.0 |
| Self-emulsifiable glyceryl stearate | 3.0 |
| Cetyl alcohol | 0.5 |
| Stearyl alcohol | 0.5 |
| Paraffin oil | 12.0 |
| Sesame oil | 10.0 |
| Stearic acid | 3.0 |
| Methyl parahydroxybenzoate | 0.2 |
| Propyl parahydroxybenzoate | 0.1 |
| Fragrance | 0.3 |
| Demineralized water q.s. for | 100 |
| EXAMPLE 3: Protective moisturizing cream | |
| Lysine lauroylmethionate | 2.3 |
| Flavonoid Extracts from green tea ("Sunphenon" of the Company Jan Dekker Int.) | 1.0 |
| Glyceryl stearate | 3.0 |
| Stearyl alcohol | 0.5 |
| Stearic acid | 2.0 |
| Perhydrosqualene | 12.0 |
| Volatile silicone oil | 5.0 |
| Methyl parahydroxybenzoate | 0.2 |
| Propyl parahydroxybenzoate | 0.1 |
| Fragrance | 0.3 |
| Demineralized water q.s. for | 100 |
| EXAMPLE 4: Protective cream for the hands | |
| Lysine lauroylmethionate | 0.345 |
| Methyl caffeate | 0.4 |
| Rutin | 0.5 |
| Sorbitan monostearate polyoxyethylenated with 20 mol of ethylene oxide | 2.0 |
| Cetyl alcohol | 1.0 |
| Isopropyl myristate | 3.0 |
| Paraffin oil | 7.0 |
| Volatile silicone oil | 7.0 |
| Methyl parahydroxybenzoate | 0.2 |
| Propyl parahydroxybenzoate | 0.1 |
| Demineralized water q.s. for | 100 |
| EXAMPLE 5: Vesicular dispersions | |
| Lysine lauroylmethionate | 0.23 |
| Methyl 2,5-dihydroxy-4-methylphenylacetate | 0.05 |
| Hydrogenated soya lecithin | 1.8 |
| Cholesterol | 0.9 |
| Collagenic palmitoyl lipacid | 0.3 |
| Glycerol | 0.3 |
| Macadamia oil | 15.0 |
| Volatile silicone oil | 10.0 |
| Carboxyvinyl polymer sold under the name of "Carbopol 940" by the Company Goodrich | 0.6 |
| Methyl parahydroxybenzoate | 0.2 |
| Triethanolamine q.s. pH = 6 | |
| Demineralized water q.s. for | 100 |

I claim:

1. A cosmetic or dermopharmaceutical composition containing, in a suitable vehicle, an antioxidizing system possessing a synergic effect consisting of the combination of lauroylmethionate of lysine, histidine or arginine and a rosemary extract having carnosic acid and carnosol.

2. The composition according to claim 1 wherein the antioxidizing system contains lauroylmethionate of lysine.

3. The composition according to claim 1 wherein the lauroylmethionate of lysine, histidine or arginine is present at a concentration between 0.02% and 5% with respect to the total weight of the composition.

4. The composition according to claim 1 wherein the rosemary extract, having carnosic acid and carnosol is present at a concentration between 0.005 and 5% by weight with respect to the total weight of the composition.

5. The composition according to claim 4 wherein the rosemary extract contains carnosic acid and carnosol and is present at a concentration between 0.1 and 5% by weight with respect to the total weight of the composition.

6. The composition according to claim 1 which further contains one oxidation-sensitive product in a proportion between 1 and 99% by weight with respect to the total weight of the composition wherein the oxidation-sensitive product is selected from the group consisting of Vitamin F and beta carotene.

7. The composition according to claim 1 which further contains additives selected from the group consisting of surface-active agents, dyes and fragrances.

* * * * *